(12) United States Patent
Miller et al.

(10) Patent No.: US 12,310,699 B2
(45) Date of Patent: May 27, 2025

(54) ACOUSTO-OPTIC HARMONIC IMAGING WITH OPTICAL SENSORS

(71) Applicant: DeepSight Technology, Inc., Los Altos, CA (US)

(72) Inventors: Scott A. Miller, Ithaca, NY (US); Danhua Zhao, San Jose, CA (US); Lan Yang, Clayton, MO (US); Jiangang Zhu, University City, MO (US)

(73) Assignee: DEEPSIGHT TECHNOLOGY, INC., Santa Clara, CA (US)

( * ) Notice: Subject to any disclaimer, the term of this patent is extended or adjusted under 35 U.S.C. 154(b) by 90 days.

(21) Appl. No.: 18/091,073

(22) Filed: Dec. 29, 2022

(65) Prior Publication Data

US 2023/0255495 A1 Aug. 17, 2023

Related U.S. Application Data

(63) Continuation of application No. PCT/US2021/039551, filed on Jun. 29, 2021.

(60) Provisional application No. 63/046,888, filed on Jul. 1, 2020.

(51) Int. Cl.
*A61B 5/00* (2006.01)

(52) U.S. Cl.
CPC .................. *A61B 5/0097* (2013.01)

(58) Field of Classification Search
CPC ........... A61B 5/0097; G01N 2291/042; G01N 2291/044; G01N 29/0654; G01N 29/12; G01N 29/2418
See application file for complete search history.

(56) References Cited

U.S. PATENT DOCUMENTS

| | | | |
|---|---|---|---|
| 5,410,516 A | * | 4/1995 | Uhlendorf ........... G01S 7/52038 367/7 |
| 6,490,039 B2 | | 12/2002 | Maleki et al. |
| 6,795,481 B2 | | 9/2004 | Maleki et al. |
| 6,861,978 B2 | | 3/2005 | Lam |
| 7,184,624 B1 | | 2/2007 | Matsko et al. |

(Continued)

FOREIGN PATENT DOCUMENTS

| | | |
|---|---|---|
| CN | 101750280 A | 6/2010 |
| CN | 112666562 A | 4/2021 |

(Continued)

OTHER PUBLICATIONS

Anvari, A. et al. (2015). "A Primer on the Physical Principles of Tissue Harmonic Imaging." RadioGraphics 35:1955-1964.

(Continued)

*Primary Examiner* — Baisakhi Roy
*Assistant Examiner* — Kaitlyn E Sebastian
(74) *Attorney, Agent, or Firm* — Kilpatrick Townsend & Stockton LLP

(57) ABSTRACT

An acousto-optic imaging system may include at least one transducer that transmits an ultrasound signal having a fundamental frequency f. The acousto-optic imaging system includes at least one optical sensor that may produce one or more optical responses upon receiving harmonic-related ultrasound echoes corresponding to the transmitted ultrasound signal. For example, the one or more optical sensors may have a bandwidth ranging from at least f/M to Nf, where M and N are integers greater than 1.

21 Claims, 10 Drawing Sheets

(56) References Cited

U.S. PATENT DOCUMENTS

| | | | |
|---|---|---|---|
| 7,545,843 B2 | 6/2009 | Armani et al. | |
| 7,781,217 B2 | 8/2010 | Armani et al. | |
| 7,914,454 B2 | 3/2011 | Weber et al. | |
| 8,493,560 B2 | 7/2013 | Shopova et al. | |
| 9,354,174 B2 | 5/2016 | Poetter et al. | |
| 9,554,774 B2 | 1/2017 | Moore et al. | |
| 9,588,061 B2 | 3/2017 | Sun et al. | |
| 9,733,125 B2 | 8/2017 | Liu et al. | |
| 9,846,126 B2 | 12/2017 | Gunn, III et al. | |
| 11,041,811 B2 | 6/2021 | Gunn, III et al. | |
| 2004/0039282 A1* | 2/2004 | Szabo | G01S 7/52038 600/437 |
| 2007/0237460 A1* | 10/2007 | Fan | G01N 21/7746 385/12 |
| 2008/0095490 A1 | 4/2008 | Ashkenazi et al. | |
| 2010/0231903 A1* | 9/2010 | Sumetsky | G01N 21/7746 264/2.7 |
| 2013/0208562 A1* | 8/2013 | Shen | G01S 7/52038 367/7 |
| 2014/0360273 A1 | 12/2014 | Zhang et al. | |
| 2016/0273943 A1 | 9/2016 | Grubel | |
| 2018/0238833 A1 | 8/2018 | Somekh | |
| 2019/0083049 A1 | 3/2019 | Byrnes et al. | |
| 2019/0083059 A1* | 3/2019 | Byrnes | H01S 3/302 |
| 2021/0181422 A1 | 6/2021 | Ciao et al. | |
| 2021/0349009 A1* | 11/2021 | Rozental | G01H 9/00 |
| 2022/0365036 A1 | 11/2022 | Yang et al. | |

FOREIGN PATENT DOCUMENTS

| | | |
|---|---|---|
| CN | 112690827 A | 4/2021 |
| CN | 113177992 A | 7/2021 |
| EP | 3 781 982 A1 | 2/2021 |
| GB | 2557913 A | 7/2018 |
| JP | 11137547 A | 5/1999 |
| JP | 11290318 A | 10/1999 |
| JP | 2005529672 A | 10/2005 |
| JP | 2009066110 A | 4/2009 |
| JP | 2010518396 A | 5/2010 |
| WO | WO-2006/001842 | 1/2006 |
| WO | WO-2007/106601 | 9/2007 |
| WO | WO-2020/221777 A1 | 11/2020 |
| WO | WO-2021/055823 | 3/2021 |
| WO | WO-2021/119182 A1 | 6/2021 |
| WO | WO-2021/202093 A1 | 10/2021 |

OTHER PUBLICATIONS

Bae et al. (2008). "A new ultrasonic Synthetic Aperture tissue Harmonic imaging system," 2008 *IEEE Ultrasonics Symposium*, pp. 1258-1261.

Bae et al. (2011). "A new extended range ultrasonic synthetic aperture tissue harmonic Imaging system," 2011 *IEEE International Ultrasonics Symposium*, pp. 401-404.

Cherin, E. et al. (2019). "*In vitro* superharmonic contrast imaging using a hybrid dual-frequency probe," Ultrasound in Med. & Biol. 45:2525-2539.

Chiou, S-Y. et al. (2007). "Comparing Differential Tissue Harmonic Imaging with Tissue Harmonic and Fundamental Gray Scale Imaging of the Liver," J. Ultrasound Med. 26:1557-1563.

Hamilton, J.D. et al. (2000). "High frequency optoacoustic arrays using etalon detection," IEEE Transactions on Ultrasonics, Ferroelectrics and Frequency Control 47:160-169.

Kim, Hyung Ham (May 2010). "Array transducers for high frequency ultrasound imaging," Dissertation, 113 total pages.

International Search Report mailed on Apr. 29, 2021, for PCT Application No. PCT/US2020/064094, filed on Dec. 9, 2020, 7 pages.

International Search Report mailed on Jan. 4, 2022, for PCT Application No. PCT/US2021/039551, filed on Jun. 29, 2021, 6 pages.

Londhe, N.D. et al. (2016). "Superharmonic Imaging for Medical Ultrasound: A review," Journal of Medical Systems. 40:279.

Madhvapathy, S. et al. (May 2021). "Ultrasound detection with silicon microring resonators," Electrical Engineering and Computer Sciences, University of California, Berkeley, Technical Report No. UCB/EECS-2021-123, 53 total pages.

Nikolov, S.I. et al. (2015). "Synthetic aperture imaging using a semi-analytic model for the transmit beams," 2015 IEEE International Ultrasonics Symposium (IUS), pp. 1-4.

Rasmussen, J.H. et al. (2012). "Implementation of tissue harmonic synthetic aperture imaging on a commercial ultrasound system," 2012 IEEE International Ultrasonics Symposium, pp. 121-125.

Rasmussen, J.H. et al. (2013). "Preliminary study of synthetic aperture tissue harmonic imaging on in-vivo data," Proceedings vol. 8675, SPIE Medical Imaging 2013: Ultrasonic Imaging, Tomography, and Therapy, 867512.

Thijssen J.M. et al. (2014). "Cardiological Ultrasound Imaging," Curr. Pharm Des. 20:6150-6161.

Written Opinion of the International Searching Authority mailed on Apr. 29, 2021, for PCT Application No. PCT/US2020/064094, filed on Dec. 9, 2020, 11 pages.

Written Opinion of the International Searching Authority mailed on Jan. 4, 2022, for PCT Application No. PCT/US2021/039551, filed on Jun. 29, 2021, 10 pages.

Yoo, G. et al. (2015). "All-Optical Ultrasound Transducer Using CNT-PDMS and Etalon Thin-Film Structure," IEEE Photonics Journal 7:1-8.

U.S. Appl. No. 62/901,883, filed Sep. 18, 2019, by Yang et al.

U.S. Appl. No. 62/945,538, filed Dec. 9, 2019, by Zhao et al.

Monifi, et al., "Ultrasound Sensing Using a Fiber Coupled Silica Microtoroid Resonator Encapsulated in a Polymer", 2013 IEEE Photonics Conference, Bellevue, WA, USA, doi: 10.1109/IPCon. 2013.6656511, 2013, pp. 2015-2016.

Wei, et al., "High-Frequency Ultrasonic Sensor Arrays Based on Optical Micro-ring Resonators", Proc. SPIE 10600, Health Monitoring of Structural and Biological Systems XII, 1060003, Mar. 27, 2018, 8 pages.

European Application No. 21765741.0, "Office Action", Dec. 11, 2024, 6 pages.

Japanese Application No. 2022-579983, "Office Action", Mar. 6, 2025, 8 pages.

* cited by examiner

ACOUSTO-OPTIC HARMONIC IMAGING WITH OPTICAL SENSORS

CROSS-REFERENCE TO RELATED APPLICATIONS

This application is a continuation of International Patent Application No. PCT/US2021/039551 filed Jun. 29, 2021, which claims priority to U.S. Patent Application No. 63/046,888 filed Jul. 1, 2020, each of which is incorporated by reference in its entirety.

TECHNICAL FIELD

The present disclosure generally relates to the field of acousto-optic imaging, and in particular to methods and devices with optical sensors for ultrasound sensing and harmonic imaging.

BACKGROUND

Ultrasound sensing is used in various industries including medical imaging, due to a number of advantages. For example, ultrasound sensing utilizes ultrasound signal, which has a remarkable penetration depth. Moreover, ultrasound imaging is known to be an advantageously non-invasive form of imaging, as it is based on non-ionizing radiation.

Conventional ultrasound sensing uses piezoelectric materials such as lead-zirconate-titanate (PZT), polymer thick film (PTF), polyvinylidene fluoride (PVDF), and capacitive micromachined ultrasonic transducer (CMUT). However, one of the challenges associated with such conventional ultrasound sensing is their narrow bandwidth. Thus, there is a need for new and improved devices and methods for ultrasound imaging modes with various frequency harmonics to obtain higher resolution, better penetration, and fewer artifacts than fundamental imaging of conventional ultrasound sensing.

SUMMARY

Generally, in some embodiments, an acousto-optic imaging system may include at least one transducer (e.g., one transducer, 10 transducers, 100 transducers, and/or the like) that transmits one or more ultrasound signals each having a respective fundamental frequency (e.g., fundamental frequency f). The at least one transducer may include a piezoelectric transducer, a capacitive micromachined ultrasonic transducer (CMUT), a polymer thick film (PTF) transducer, a photoacoustic transducer, a piezoelectric micromachined ultrasound transducer (PMUT), and/or the like. The acousto-optic imaging system includes at least one optical sensor (e.g., one optical sensor, 10 optical sensors, 100 optical sensors, and/or the like) with a broadband acoustic response that produces one or more optical responses upon receiving fundamental frequency, super-harmonic, ultra-harmonic, subharmonic, or differential harmonic ultrasound echoes corresponding to the transmitted ultrasound signal(s).

The fundamental frequency can be defined as the frequency of the original transmitted ultrasound signal. The super-harmonic can be defined as an integer multiple of the original transmitted frequency or the fundamental frequency. For example, the second super-harmonic is 6 Megahertz (MHz) when the fundamental frequency is 3 MHz. The ultra-harmonic can be defined as a frequency that is higher than the fundamental frequency, but not a super-harmonic. For example, one possible ultra-harmonic is 4.5 MHz when the fundamental frequency is 3 MHz. The sub-harmonic can be defined as a fraction of the original transmitted frequency or the fundamental frequency. For example, one possible sub-harmonic is 1.5 MHz when the fundamental frequency is 3 MHz. When transmitted ultrasound signals (e.g., transmitted by the at least one transducer) include more than one frequency (e.g., 2 frequencies), in some instances, a nonlinear medium, imaged by the acousto-optic imaging system, may also produce so-called differential harmonics. For example, if the transmitted ultrasound signals include both 3 MHz and 5 MHz frequencies, then one possible differential harmonic can include 5−3=2 MHz frequency. In some instances, the at least one optical sensor (e.g., a whispering gallery mode (WGM) optical resonator, microbubble resonator, microsphere resonator, micro disk resonator) may include a closed loop of a material that is optically transparent to the one or more optical responses with an acoustic response bandwidth ranging from at least f/M to Nf, where M and N are integers greater than 1. By leveraging such broadband acoustic responses of the at least one optical sensor, the acousto-optic imaging system may use a fundamental frequency, subharmonic, ultra-harmonic, super-harmonic, and/or differential harmonics of the ultrasound signal. As a result, such an apparatus may be less complex and be easily mass-produced in a cost-efficient manner.

In some embodiments, the at least one optical sensor may produce at least a portion of the one or more optical responses upon receiving ultrasound echoes having a super-harmonic frequency of at least Qf, where Q is an integer 3 or greater (e.g., super-harmonic frequencies of 3f, 6f, 11f, and/or the like). Furthermore, the at least one optical sensor may produce at least a portion of the one or more optical responses upon receiving ultrasound echoes having a frequency of 2f or f. Similarly, the at least one optical sensor may produce at least a portion of the one or more optical responses upon receiving ultrasound echoes having a sub-harmonic frequency of f/R, where R is an integer 2 or greater (e.g., subharmonic frequencies of f/2, f/5, f/8, and/or the like).

In some embodiments, the at least one optical sensor may produce at least a portion of the one or more optical responses upon receiving ultrasound echoes having an ultra-harmonic frequency of at least Qf, where Q is a non-integer number greater than 1 (e.g., ultra-harmonic frequencies of 1.5f, 2.5f, 3.33f, and/or the like). Similarly, the at least one optical sensor may produce at least a portion of the one or more optical responses upon receiving ultrasound echoes having a subharmonic frequency of f/R, where R is a non-integer number greater than 1 (e.g., subharmonic frequencies of f/1.5, f/2.75, f/4.33, and/or the like).

In some embodiments, the at least one transducer may generate a first ultrasound signal having a first fundamental frequency $f_1$ and a second ultrasound signal having a second fundamental frequency $f_2$. Moreover, the at least one optical sensor may produce at least a portion of the one or more optical responses upon receiving ultrasound echoes that correspond to a frequency of one or more linear combinations $nf_1+mf_2$. The parameters n and m represent integers that are selected such that the linear combination $nf_1+mf_2$ becomes a positive number. The parameters n and m, however, may include negative integers or positive integers. Therefore the linear combination may be a difference between a multiple of the first fundamental frequency and a multiple of the second fundamental frequency, or may be a summation of the multiple of the first fundamental frequency and the multiple of the second fundamental frequency.

In some embodiments, the acousto-optic imaging system may include a computer-readable medium that stores code representing instructions to generate an image based on the one or more optical responses of the at least one optical sensor. The computer-readable medium may, for example, provide instructions to generate the image by calculating a magnitude of each ultrasound echo at the at least one optical sensor based on the change, and further executing code to convert the magnitude of each ultrasound echo to a pixel value for display.

In some embodiments, the change may indicate a spectral shift. The at least one optical sensor may be highly sensitive such that each optical response includes at least one spectral resonance feature with a full-width at half-maxima (FWHM) that is smaller than the spectral shift. In some instances, the at least one optical sensor may include several spectral response features (e.g., 10 s of spectral response features, 100 s of spectral response features, and/or the like) that have a high quality factor (Q factor). Each of the several spectral response features may be smaller than the spectral shift detected to form the image using the at least one optical sensor.

In some embodiments, the at least one optical sensor may have an effective refractive index and a wall thickness that enable propagation of a set of whispering gallery modes (WGMs) in the at least one optical resonator. Furthermore, the at least one optical sensor may be coupled to one or more optical waveguides (e.g., optical fibers, photonic integrated circuit waveguides, and/or the like) to propagate the plurality of optical signals to one or more optical detectors.

In some embodiments, the change in spectral response features of the at least one optical sensor can be caused by a change in the effective refractive index of at least one optical sensor due to a photo-elastic effect of the at least one optical sensor upon receipt of the ultrasound echoes. In some embodiments, the at least one optical sensor may be embedded in a polymer structure that has an effective refractive index lower than the effective refractive index of the at least one optical sensor.

In some embodiments, a method of acousto-optic imaging may include transmitting to a medium an ultrasound signal via at least one transducer that has a fundamental frequency f. Furthermore, the method may further include producing one or more optical responses via at least one optical sensor upon receiving harmonic or subharmonic ultrasound echoes corresponding to the transmitted ultrasound signal. The at least one optical sensor may have a bandwidth ranging from at least f/M to Nf, where M and N are integers greater than 1.

In some embodiments, the medium may include a nonlinear medium. In particular, in some embodiments, the medium may include a biological tissue.

In some embodiments, a method of acousto-optic imaging may include transmitting to a medium one or more ultrasound signals having one or more fundamental frequencies. The one or more signals may be incident on the medium and result in ultrasound echoes that can form a visual representation of the medium. Furthermore, the method may include detecting at least one change in an optical response of one or more optical detectors, where the at least one change is produced upon receiving the ultrasound echoes. A portion of the received ultrasound echoes may have a frequency that is a super-harmonic frequency, an ultra-harmonic frequency, a subharmonic frequency, or a linear combination of the one or more fundamental frequencies. The method may also include generating an image of the medium based on the detected change in the optical response.

DETAILED DESCRIPTION

Non-limiting examples of various aspects and variations of the invention are described herein and illustrated in the accompanying drawings.

As described herein, an acousto-optic imaging system based on optical sensors can simultaneously achieve high sensitivity and broadband response at levels not found in ultrasound systems that sense ultrasound echoes based on traditional transducers such as, for example, piezoelectric or CMUT transducers. Using this high sensitivity and the broadband response, an acousto-optic imaging system can detect a wide range of acoustic frequencies to generate an ultrasound image of a medium with higher penetration depth and/or higher spatial resolution than images generated by traditional transducers.

Harmonic Acousto-Optic Imaging System

Figure 1:
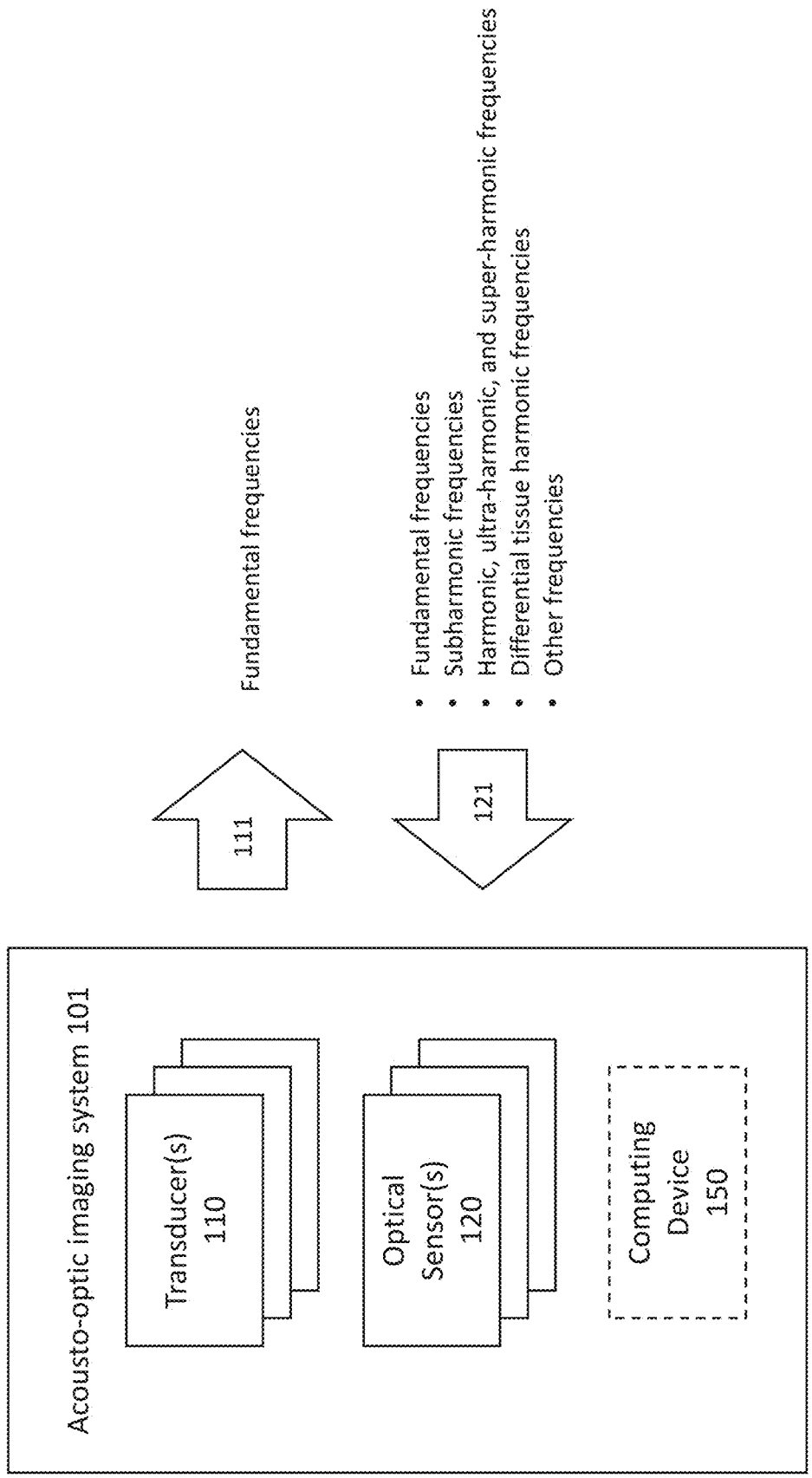
FIG. 1 illustrates a schematic of an exemplary acousto-optic imaging system.

As shown in FIG. 1, an acousto-optic imaging system 101 may include one or more transducers 110 and one or more optical sensors 120. A transducer 110 is configured to generate and/or transmit an ultrasound signal 111 that has a fundamental frequency f toward a medium for imaging. The medium can be a nonlinear medium such as for example, a body tissue. An optical sensor 120 is configured to produce optical responses upon receiving ultrasound echoes 121 reflected in response to interactions of the ultrasound signal 111 with the medium. In some variations, propagation of the ultrasound signal 111 through the medium may produce echoes at various frequencies including the fundamental frequency f and harmonic-related frequencies including one or more subharmonic frequencies, one or more ultra-harmonic frequencies, one or more harmonic and/or superharmonic frequencies, and/or the like. As further described below, the acousto-optic imaging system 101 may be configured to detect a wide range of frequencies including these specialized harmonic-related frequencies, which enables it to universally perform various harmonic-related imaging, including harmonic imaging, ultra-harmonic imaging, superharmonic imaging, subharmonic imaging, and the like for an advantageously broad range of imaging modes and functionalities. The use of one or more optical sensors in a single acousto-optic imaging system is also advantageous because it enables an imaging system with fewer ultrasound probes, thereby leading to reduced complexity and improved efficiency of the acousto-optic imaging system.

Transducers

The transducer(s) 110 for generating and/or transmitting an ultrasound signal may include for example, a piezoelectric transducer(s), a lead zirconate titanate (PZT) transducer(s), a polymer thick film (PTF) transducer(s), a polyvinylidene fluoride (PVDF) transducer(s), a capacitive micromachined ultrasound transducer (CMUT), a piezoelectric micromachined ultrasound transducer (PMUT), a photoacoustic transducer(s), a transducer(s) based on single crystal materials (e.g., $LiNbO_3$(LN), $Pb$ $(Mg_{1/2}Nb_{2/3})$—$PbTiO_3$ (PMN-PT), and $Pb$ $(In_{1/2}Nb_{1/2})$—$Pb(Mg_{1/2}Nb_{2/3})$—$PbTiO_3$ (PIN-PMN-PT)), and/or any suitable component for generating and/or transmitting an ultrasound signal. Furthermore, in some variations the transducer(s) 110 may be configured to detect ultrasound echoes at certain limited frequencies for use in generating images (e.g., in combination with signals from the optical sensor(s) 120).

Optical Sensors

The optical sensor(s) 120 may be suitable for high sensitivity, broad bandwidth applications including high sensitivity acousto-optic imaging systems. In some instances, for example, each optical sensor 120 can include a closed loop of a transparent medium that allows some permitted frequencies of light to continuously propagate inside the closed loop, and to store optical energy of the permitted frequencies of light in the closed loop. For example, the optical sensor 120 permits a propagation of whispering gallery modes (WGMs) traveling the concave surface of the optical sensor 120 and corresponding to the permitted frequencies to circulate the circumference of the sensor. Each mode from the WGMs corresponds to propagation of a frequency of light from the permitted frequencies of light. The aforementioned WGM resonators could appear in the form of spheres, disks, rings, bubbles, cylinders, and/or toroids, for example. They could be made of optical transparent materials with low loss at the wavelength of light propagating in the resonator, such as silica and silicon in the infrared spectral window, or chalcogenide in the mid-infrared window, for example.

The optical sensor(s) 120 have high sensitivity and broad bandwidth due at least in part on having high quality factor, in that they advantageously allow the permitted frequencies of light to stay in a closed loop of each optical sensor 120 for a long period of time. The permitted frequencies of light of an optical sensor 120 may be based at least in part on geometrical parameters of the optical sensor 120, refractive index of the transparent medium, and refractive indices of an environment surrounding the optical sensor 120. The quality factor described herein is determined by the loss experienced by light propagating in the resonators; the loss may come from materials absorption, material and structural inhomogeneity, radiation dissipation, light scattering, coupling rate to external waveguides.

Each optical sensor 120 may be coupled to the outside world to receive light, to transmit light, and to be useful in practice (e.g., for an ultrasound imaging or other sensing application in an acousto-optic imaging system). Acousto-optic imaging systems based on the optical sensor(s) 120 may directly detect ultrasonic waves through the photoelastic effect and/or physical deformation of the sensor(s) in response to the ultrasonic waves (e.g., ultrasonic echoes). For example, in the presence of ultrasonic (or any pressure) waves, the WGMs traveling a resonator may undergo a spectral shift caused by changes in the refractive index and shape of the resonator. The spectral change can be easily monitored and analyzed in spectral domain and light transmission intensity to and from the optical sensor(s) 120. Additional spatial and other information can furthermore be derived by monitoring and analyzing the optical sensor(s) 120.

Examples of Optical Sensors

As described above, optical sensors have high quality factor and broadband spectral response and various other beneficial features, which are advantageous for use in applications such as ultrasound sensing and/or ultrasound imaging. Optical sensors may include, for example, an optical resonator(s) (e.g., a WGM optical resonator(s)), a microbubble resonator(s), a fiber-based resonator(s), an integrated photonic resonator(s), a micro-disk resonator(s), and/or the like.

Figure 5B:
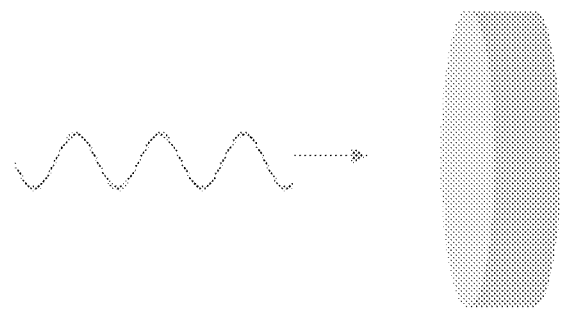
FIG. 5B is a schematic description of exemplary geometrical shape of an optical microdisk resonator.
Figure 5A:
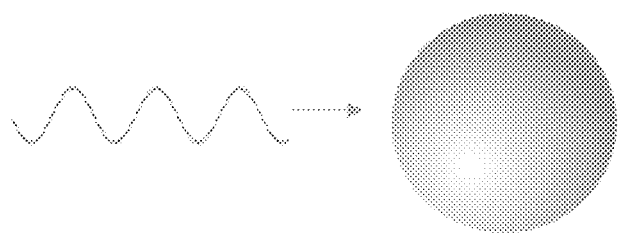
FIG. 5A is a schematic description of exemplary geometrical shape of an optical microbubble/microsphere resonator.

As shown in FIG. 5A, at least one optical sensor may be a whispering galley mode (WGM) optical resonator such as an optical microbubble resonator. The optical microbubble resonator can be made of an optically transparent material such as, for example, glass, transparent polymer, silicon nitride, titanium dioxide, or any other material that is suitably optically transparent at an operation wavelength of the optical microbubble resonator. The optical microbubble resonator includes an outer microbubble surface with a radius (R) and an inner microbubble surface with a radius (r), thereby defining a resonator wall thickness equivalent to (R-r). A set of resonant frequencies (due to propagation of a set of WGMs) of the optical microbubble resonator can have high quality factors suitable for highly sensitive acousto-optic sensing probes. In general, the sensitivity of WGM optical resonators can be improved by increasing the quality factor of the WGM optical resonator. In particular, in such implementations, the sensitivity can be controlled by a wall thickness (R-r) of the optical microbubble resonator. When used as ultrasound detectors, the optical microbubble resonator can have a low noise equivalent pressure and a broadband operation bandwidth as described in further detail herein.

In some implementations, the optical sensor(s) may include sensing nodes formed at a cross-section of optical fibers and optical waveguides when light propagating in the optical waveguides couples in the optical fibers and propagates in circumferences of the optical fibers. In some variations the optical sensor(s) may include an integrated photonic optical resonator. For example, in some variations the optical sensor(s) may be similar to any of the WGM optical resonators described in PCT Application No. PCT/US2020/064094 and PCT Application No. PCT/US2021/022412, each of which is incorporated herein in its entirety.

The space inside and/or around the optical sensor(s) may be filled with a polymer structure such as an ultrasonic enhancement material. For example, the optical sensors may be filled with polyvinylidene fluoride, parylene, polystyrene, and/or the like. The ultrasonic enhancement material can increase sensitivity of the optical sensor(s). For example, the ultrasonic enhancement material can have a relatively high elasto-optic coefficient, such that in response to the optical sensor(s) receiving a set of ultrasound echoes, the refractive index of the ultrasonic enhancement material changes more than the refractive index of the material of a material(s) of the optical sensor(s) (e.g., upon receiving a mechanical stress or strain induced by the set of ultrasound echoes). An effective refractive index of the polymer structure may be lower than the effective refractive index of the optical sensor(s).

As shown in FIG. 5B, an optical sensor may be a micro-disk resonator. The micro-disk resonator can be made of an optically transparent material and/or an optically opaque material such as, for example, glass, transparent polymer, silicon nitride, titanium dioxide, silicon, or any other material that is suitable for propagation of light in, on, and/or about the micro-disk resonator. In some variation the micro-disk resonator may be made of a combination optically transparent materials and optically opaque materials. A set of resonant frequencies (due to propagation of a set of WGMs) of the micro-disk resonator can have high quality factors suitable for highly sensitive acousto-optic sensing probes.

In some variations, sensing of ultrasound signals by an optical sensor (e.g., a WGM optical resonator) described above happens because a pressure of ultrasound at the optical sensor may cause a change in the index of refraction of a material included in the optical sensor. Thickness of WGM modes propagating in, on, and/or about the optical sensor, and modal distribution in, on, and/or about the optical sensor may be considered as spatial window for ultrasound sensing. A convolution of the ultrasound signals and the spatial window may result in changes in optical response of the optical sensor.

Figure 6A:
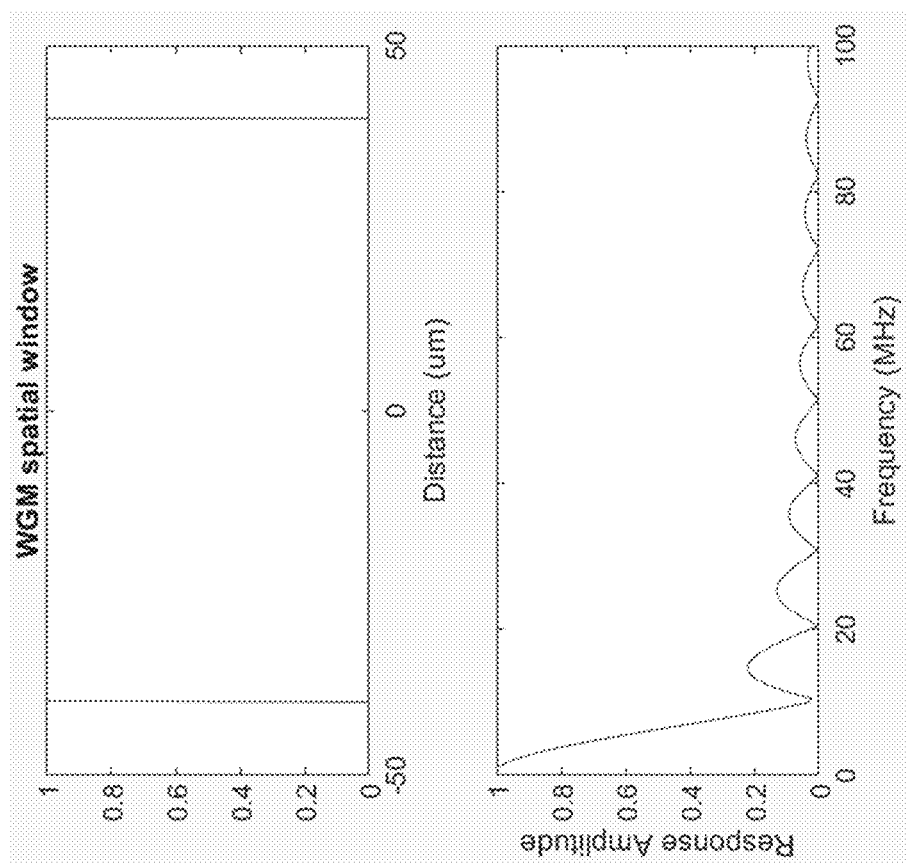
FIGS. 6A-6C are exemplary spectral responses of a set of optical sensors.
Figure 6B:
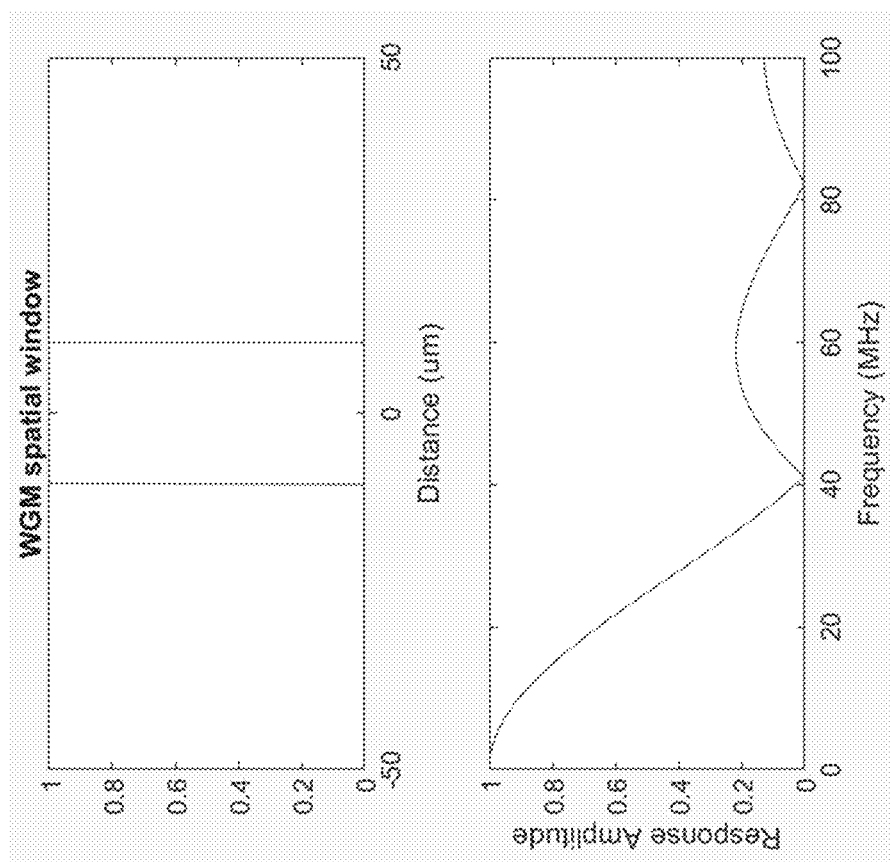
Figure 6C:
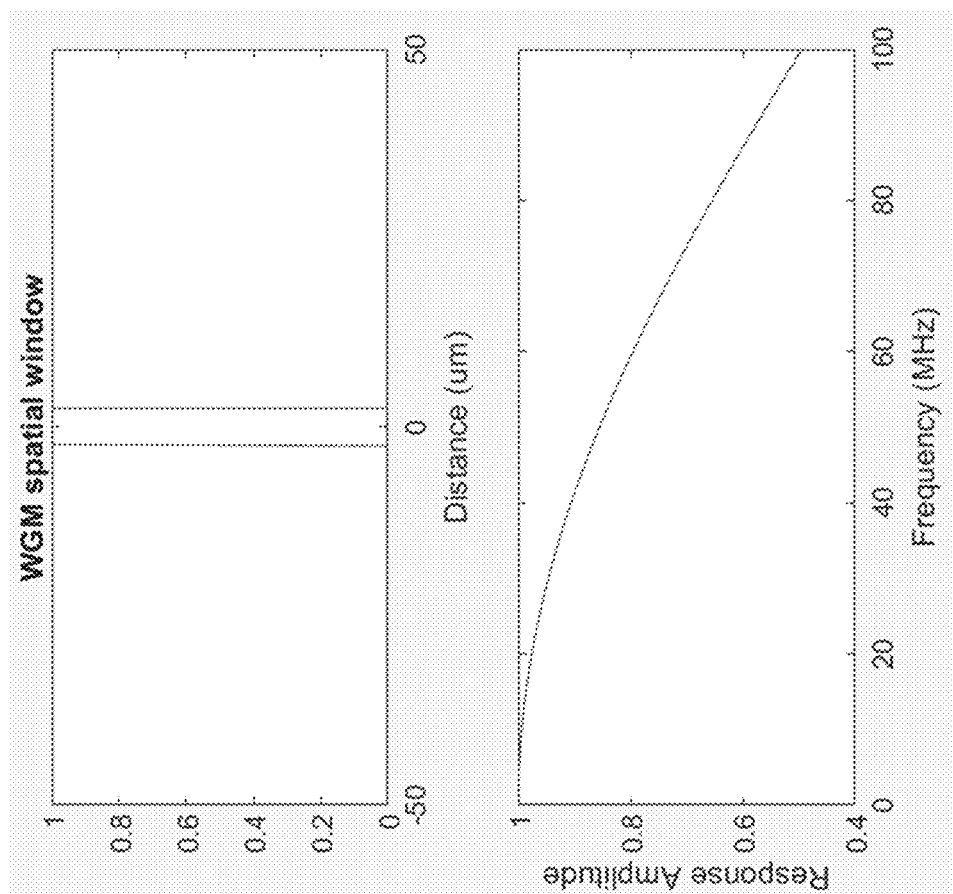

FIGS. 6A-6C are exemplary spectral responses of a set of optical sensors (e.g., WGM optical resonators). The upper plot of each of FIGS. 6A-6C shows a generally rectangular spatial window corresponding to physical dimension/distribution of an optical WGM resonance mode. In some instances, a spectral response in frequency domain of an incoming ultrasound echo may be convolved with the rectangular spatial window. Convolving the spectral response with the rectangular spatial window results in a sinc function, as shown in the lower plot of each of FIGS. 6A-6C. The sinc function is a Fourier Transform of each rectangular spatial window (i.e., rectangular function). Different lengths of each rectangular spatial window result in different spectral responses in frequency domain as shown in the lower part of each of FIGS. 6A-6C. In some variations, the bandwidth of the set of optical sensors (or any sensor for that matter) may be defined as a frequency range in which an amplitude of the spectral response is above a certain threshold (e.g., 0.5). A comparison of FIGS. 6A-6C shows that wider bandwidths (broadband response) may be achieved by setting the rectangular spatial window of a WGM optical resonator narrow. In contrast, a comparison of FIGS. 6A-6C shows that narrow bandwidths may be achieved by setting the rectangular spatial window of the WGM optical resonator large. For narrow WGM optical resonator structures, as shown in FIG. 6B, spatial distributions of WGM resonance modes may be restricted by the geometry of the WGM optical resonator. For larger WGM optical resonator structures, as shown in FIG. 6A, spatial distributions of WGM resonance modes may be less restricted by the geometry of the WGM optical resonator and may potentially vary considerably. Different orders of WGM resonance modes may have different thicknesses or distribution within the structure.

In some variations, other spatial windows (e.g., a Gaussian window(s), a Hamming window(s), a Kaiser window, a concave function window, and/or the like) may be convolved with the spectral response in frequency domain of the incoming ultrasound echo. For example, in some instances, a Kaiser window may be convolved with the spectral response in frequency domain of the incoming ultrasound echo. The Kaiser window includes a first parameter M and a second parameter b. The first parameter M determines the width while the second parameter b controls the shape. In some instances, when the second parameter b=0, the Kaiser window may represent a rectangular window. In some instances, when the second parameter b=4.86, the Kaiser window may represent a Hamming window. However, it should be understood that the spectral responses described above are only examples, and in other variations, the set of one or more optical sensors may have any suitable spectral response.

The bandwidth of the optical sensor may be adjusted by choosing optical modes propagating within the optical sensor having different spatial distributions. For example, fundamental modes that are mostly confined in the equatorial plane of optical sensors may provide a broadband response. In contrast, high-order modes with larger spatial distributions may have a narrowband response. The broadband response of the optical sensor may enable the acousto-optic imaging system to monitor ultrasound echoes with the same or similar frequency as a transmitted ultrasound signal with a fundamental frequency f, a subharmonic frequency (e.g., f/2), and/or superharmonic signals (e.g., 2f). In some instances, high-order modes with the narrowband response may be used to focus on signals within a particular band of interests within the fundamental frequency f of a transducer transmitting the ultrasound signal, with additional improved spectral sensitivity. In some variations, the ultrasound bandwidth of the optical sensor may be adjusted by controlling the geometry of the optical sensor. In some implementations, stronger optical (i.e., optical mode) confinement in the optical sensor and along a direction of propagation of ultrasound echoes may result in broader bandwidth of spectral response in the optical sensor. For example, a micro-disk resonator with tighter spatial confinement to light fields in along direction of propagation of ultrasound echoes normal to the micro-disk resonator may provide a broader bandwidth than in an optical microbubble resonator.

Computing Device

In some variations, the acousto-optic imaging system 101 may include a computing device 150 to process and generate an image based on one or more optical responses of the optical sensor(s) 120. In some implementations, each optical sensor is coupled to one or more optical waveguides configured to propagate the one or more optical responses to one or more optical detectors. In some implementations, the one or more detectors convert the one or more optical responses to electrical signals that are then sent to the computing device 150. In some instances, the one or more optical detectors may be included in the acousto-optic imaging system 101.

In some implementations, the computing device 150 may include a memory, a communication interface, and a processor (not shown). The communication interface may transmit/receive data to various internal components of the computing device 150 (e.g., the memory, the processor) or external components of the computing device 150 (e.g., the transducer(s) 110, the optical sensor(s) 120). The communication interface may receive the electrical signals from the one or more optical detectors and transmit them to the memory and/or the processor. The memory may store data based on the electrical signals. The processor may include, for example, a hardware based integrated circuit (IC) or any other suitable processing device configured to run and/or execute a set of instructions or code to generate the image based on the one or more optical responses.

In some implementation, the computing device 150 processes and generates the image based on a change in the one or more optical responses of the optical sensor(s) 120. Each optical response includes at least one spectral resonance feature that can be characterized/described by a full-width at half-maxima (FWHM) and/or by quality factor (Q factor) of the spectral resonance feature. The change can be a change in amplitude of the one or more optical responses or a change in resonance frequency of the one or more optical responses. The change can be indicative of magnitude of each ultrasound echo, therefore the computing device 150 may calculate a magnitude of that ultrasound echo at a location of the optical sensor 120 based on the change. Additionally or alternatively, the change may be due to a change in an effective refractive index of at the optical sensor 120 due to a photo-elastic effect on the optical sensor 120 upon receipt of the ultrasound echoes. As a result of the change in the effective refractive index, the resonance frequency changes by a spectral shift. An optical sensor 120 is very sensitive to ultrasound echoes in the sense that the FWHM of the at least one spectral feature is smaller than the spectral shift. The computing device 150 may further associate the magnitude of each ultrasound echo to the location of the optical sensor(s) 120. By iterating the above process in various manners (e.g., raster scanning, parallel processing, etc.), the computing device 150 may map a set of magnitudes mapped to a set of locations to generate the image.

Operation

As described above, the acousto-optic imaging system 101 may be configured to perform ultrasound imaging across a wide range of frequencies. In operation, the transducer(s) 110 (e.g., a piezoelectric transducer(s)) can be used to generate an ultrasound signal (e.g., an ultrasound pulse(s), an ultrasound sinusoidal wave(s), and/or the like) having at least one fundamental frequency f. The optical sensor(s) 120 (e.g., WGM optical resonator(s) with improved sensitivity and expanded bandwidth relative to the at least one transducer 110) may be used to detect ultrasound echoes corresponding to the ultrasound signals at frequencies less than, equal to, and/or greater than the fundamental frequency. Therefore, incorporation of the optical sensor 120 may enable the acousto-optic probes described herein to detect and generate images from harmonic-related modes of the fundamental frequency f (e.g., including subharmonic frequencies, and/or ultra-harmonic and/or super-harmonic frequencies, and/or differential frequencies), as further described below. By enabling detection and image generation from such harmonic-related frequencies, the optical sensor 120 may significantly increase the resolution and contrast of medical ultrasound imaging achieved by the acousto-optic imaging system 101.

Fundamental Imaging

In some variations, the acousto-optic imaging system 101 can perform at least fundamental imaging (FI), which is a form of ultrasound imaging based on reflected echoes having the same frequency as the fundamental frequency f of the corresponding transmitted ultrasound signal. The fundamental frequency f of the transmitted ultrasound signal is often chosen with a trade-off between penetration depth and spatial resolution. For example, for imaging deep tissues, the fundamental frequency f of an ultrasound probe may be determined such that the ultrasound signal can penetrate deeper in tissue, but the resulting image will have low spatial resolution. In another example, for high resolution imaging, the fundamental frequency f of an ultrasound probe may be determined such that wavelength of transmitted ultrasound signals can resolve detailed spatial features in the tissue, but only at shallow tissue depths. In other words, because the transmission frequency sacrifices either penetration depth or spatial resolution, fundamental imaging may have limited applications. However, unlike traditional systems, the acousto-optic imaging system 101 can easily be configured to additionally or alternatively detect other specialized frequencies to improve both penetration depth and spatial resolution of ultrasound imaging compared to fundamental imaging.

Harmonic, Super-Harmonic, and Ultra-Harmonic Imaging

In some variations, the acousto-optic imaging system 101 alternatively or in addition to fundamental imaging may perform tissue harmonic imaging (THI). THI involves detecting and imaging based on frequencies of equal to 2f (second harmonic frequency). Compared to fundamental imaging (FI) based on the fundamental frequency, THI results in fewer artifacts in a produced image, because harmonic waves are predominately generated in the main beam and not side lobes, and thus harmonic imaging is less sensitive to clutter and off-axis scattering events. Also, since the harmonic fields build up progressively (that is, increasing harmonic wave energies are produced with increasing depth), the effects of reverberation and near-field noise in an image produced by THI may be reduced.

In some variations, the acousto-optic imaging system 101 alternatively or in addition to fundamental imaging and/or THI performs super-harmonic imaging (SHI). SHI involves detecting superharmonic frequencies of at least Qf, where (is an integer 3 or greater. Benefits of harmonic imaging include: improved ultrasound imaging resolution, better signal-to-noise ratio (SNR), reduced speckle noise, and/or increased penetration depth.

In some variations, the acousto-optic imaging system 101 alternatively or in addition to fundamental imaging, THI, and/or SHI may perform ultra-harmonic imaging (UHI). UHI involves detecting ultra-harmonic frequencies of at least Pf, where P is a non-integer greater than 1 (e.g., a non-integer rational number greater than 1). Benefits of ultra-harmonic imaging may include: an improved ultrasound imaging resolution, a better signal-to-noise ratio (SNR), a reduced speckle noise, and/or an increased penetration depth.

Traditional ultrasound systems fail to benefit from advantages of THI, SHI, and/or UHI for reasons including bandwidth limitations and sensitivity limitations of traditional transducers. The bandwidth limitations of traditional transducers reduce (cut off) higher frequency detection. Moreover, the sensitivity limitations reduce detection sensitivity of the traditional transducers to lower energy intensity of ultrasound echoes of higher harmonic frequencies. In contrast, the acousto-optic imaging system 101 with the optical sensor(s) 120 has expanded bandwidth and improved sensitivity relative to the at least one transducer 110 to perform all THI, SHI, and UHI without the drawbacks of traditional systems.

Subharmonic Imaging

In some variations, the acousto-optic imaging system 101 may, alternatively or in addition to fundamental imaging, THI, and/or SHI, perform subharmonic imaging. Subharmonic imaging employs subharmonic frequencies fQ where Q is an integer and f is the fundamental frequency. Use of subharmonic frequencies provides better lateral resolution. Additionally, subharmonic imaging may provide improved blood-to-tissue contrast to clearly show vascular information from the surrounding tissue, which is difficult to achieve with traditional ultrasound imaging systems. With the expanded bandwidth and improved sensitivity relative to the at least one transducer 110, the acousto-optic imaging system 101 with the optical sensor(s) 120 can collect/receive sufficient information from the ultrasound echoes at subharmonic (lower) frequencies.

Differential Tissue Harmonic Imaging

In some variations, the acousto-optic imaging system 101 can alternatively or in addition to fundamental imaging, THI, SHI, UHI, and/or subharmonic imaging perform differential tissue harmonic imaging (DTHI). The acousto-optic imaging system 101 may use multiple fundamental frequencies $f_1, f_2 \ldots f_n$ and generate one or more ultrasound image based on a arithmetic relation between the multiple fundamental frequencies such as, for example, $k_{1f1} + k_{2f2} \ldots + k_{nfn}$, where $k_1, k_2, \ldots k_n$ are integer numbers. Use of DTHI frequencies can provide a variety of new and unexplored imaging modes that may span from frequencies lower than a subharmonic frequency and higher than a frequency used in SHI. Such broadband frequency response is challenging to achieve with traditional ultrasound imaging systems Therefore, use of the acousto-optic imaging system 101 with the optical sensor(s) 120 can provide imaging DTHI frequencies with a variety of advantages including higher resolution, better penetration, and fewer artifacts than potentially FI, THI, SHI, UHI, and/or subharmonic imaging.

Figure 3A:
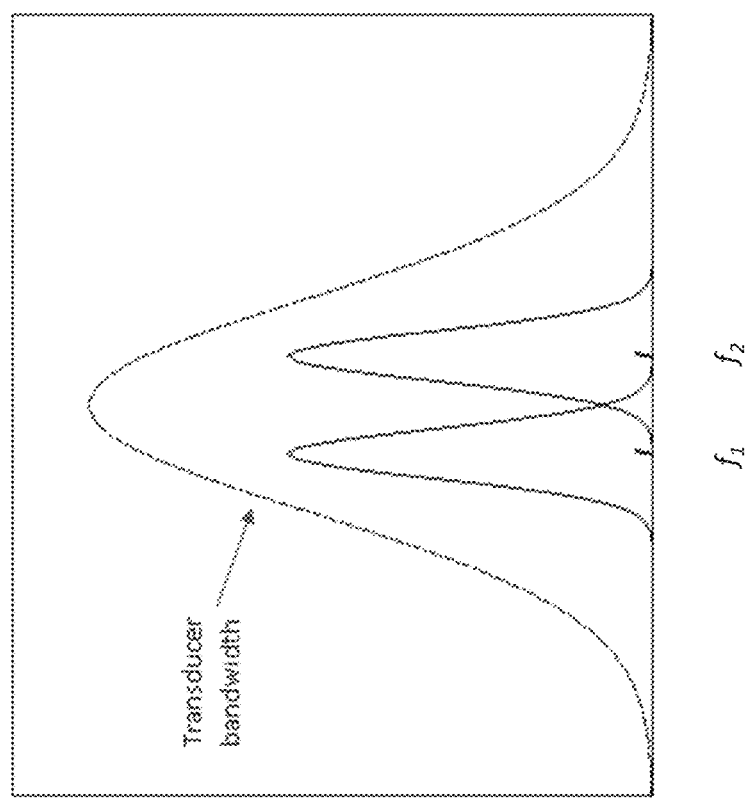
FIG. 3A is an exemplary spectral response of a transducer.
Figure 3B:
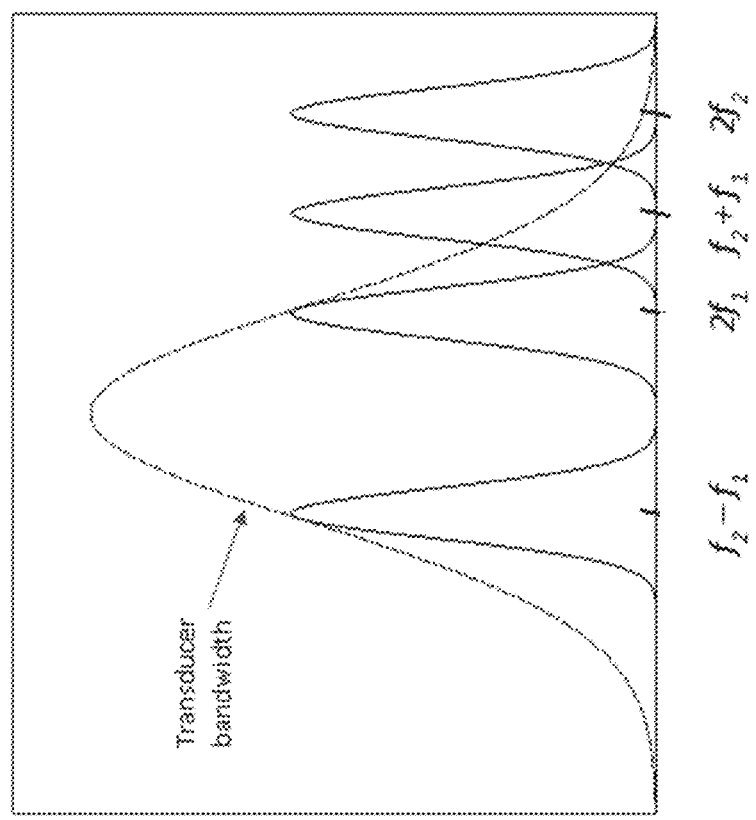
FIG. 3B is an exemplary spectral response of a transducer.
Figure 3C:
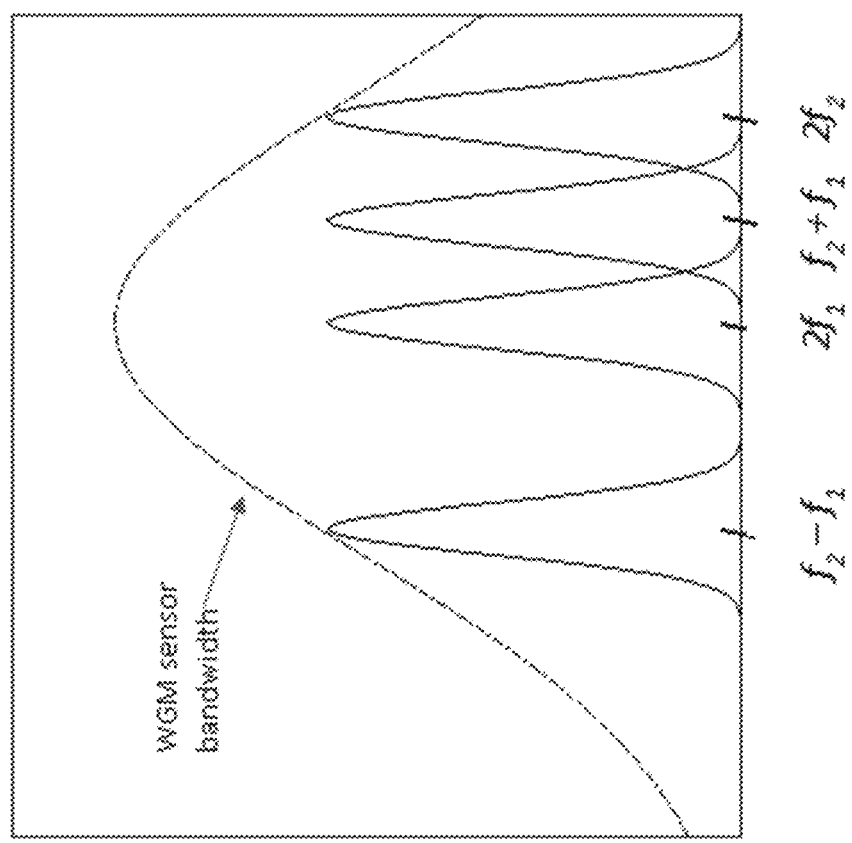
FIG. 3C is an exemplary spectral response of an optical sensor.

In some implementations, one or more transducers 110 may generate and/or transmit a set of ultrasound signals 111 that includes a first fundamental frequency $f_1$ and a second fundamental frequency $f_2$ (as shown in FIG. 3A) toward the medium for imaging. The one or more transducers 110 may only detect a narrow bandwidth of harmonic frequencies relating to the first fundamental frequency and/or the second harmonic frequency ($f_2-f_1$ and $2f_1$, as shown in FIG. 3B), thereby failing to detect valuable imaging information from other DTHI-related frequencies (e.g., $f_2+f_1$ and $2f_2$). However, as shown in FIG. 3C, the one or more optical sensors 120 may have a bandwidth that more broadly detects a selection of one or more linear combinations $mf_1+nf_2$, where m and n are integers such that $mf_1+nf_2$ becomes a positive number (as shown in FIG. 3C). Accordingly, use of optical sensors 120 to detect frequencies (e.g., $f_2+f_1$ and $2f_2$) not otherwise detectable by traditional transducers can greatly enhance ultrasound imaging capabilities. In other words, the sum and the absolute difference of the first fundamental frequency and the second fundamental frequency ($|f_2+f_1|$ and $|f_2-f_1|$, respectively) can be detected for enhanced ultrasound imaging using the acousto-optic imaging system 101.

For example, the first fundamental frequency $f_1$ can be 2 MHz and a second fundamental frequency $f_2$ can be 5 MHz and m and n can be a positive integer and a negative integer of 6 and −1. As a result, the linear combination of $mf_1+nf_2$ becomes 7 MHz which is within the bandwidth of and is detected by the at least one optical sensor 120.

For example, the first fundamental frequency $f_1$ can be 3 MHz and a second fundamental frequency $f_2$ can be 2.5 MHz and m and n can be both positive integers of 1 and 5. As a result, the linear combination of $mf_1+nf_2$ becomes 15.5 MHz which is within the bandwidth of and is detected by the at least one optical sensor 120.

It should be understood that either one of the first fundamental frequency $f_1$ and the second fundamental frequency $f_2$ may additionally or alternatively form the basis for fundamental imaging, harmonic imaging, super-harmonic imaging, ultra-harmonic imaging, and/or subharmonic imaging. For example, one or more optical sensors 120 may detect a selection of or all harmonic-related frequencies of the first fundamental frequency $f_1$ including: $f_1/Q$, $f_1/2$, $f_1/2$, $f_1$, $2f_1$ . . . and/or $Rf_1$, where Q and R are positive numbers including integers greater than 1. Additionally or alternatively, one or more optical sensors 120 may detect a selection or all harmonic frequencies of the second fundamental frequency $f_2$ including: $f_2/S$, $f_2/2$, $f_2$, $2f_2$ . . . and/or T $f_2$, where S and T are positive numbers including integers greater than 1.

Figure 2:
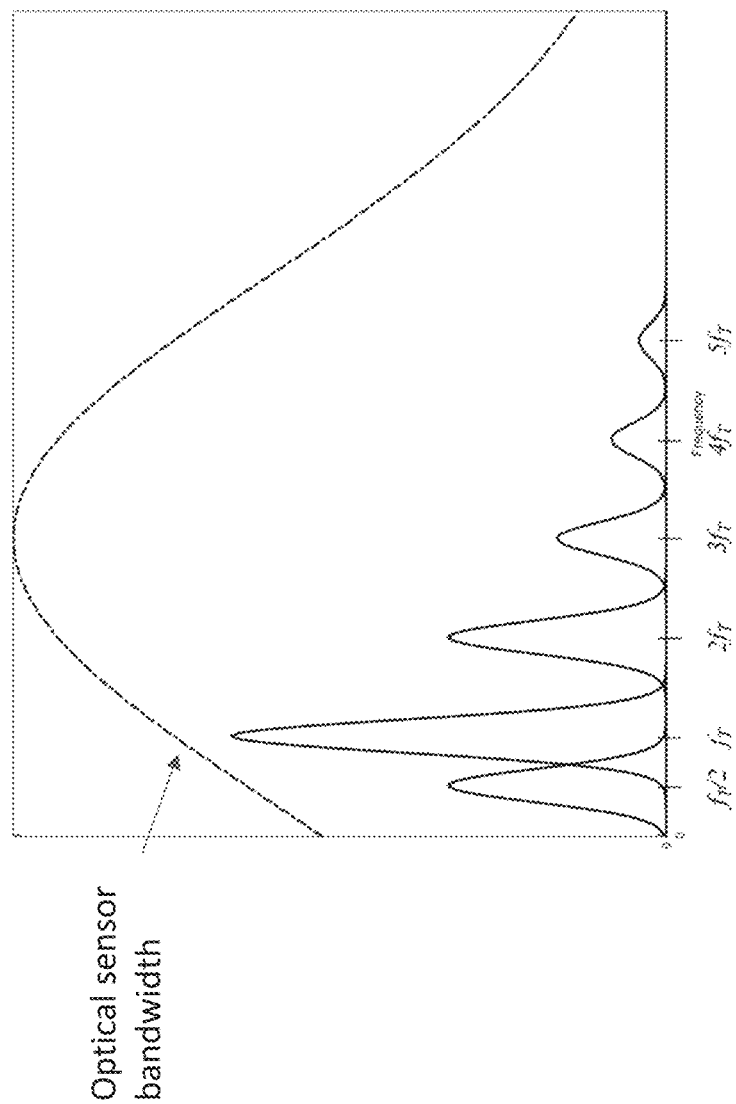
FIG. 2 is an exemplary spectral response of an optical sensor.

In some variations, while the transducer(s) 110 may be used for generating/transmitting the ultrasound signal 111 to a medium for acousto-optic imaging, only the optical sensor(s) 120 may be used to detect the acoustic echoes (instead of both transducer(s) 110 and optical sensor(s) 120). The optical sensor(s) 120 may have a bandwidth that is broad enough to detect a selection or all frequencies of the ultrasound echoes 121 including: f/Q, f/2, f, 2f, 3f, 4f, 5f . . . and/or Rf where (and R are positive numbers including integers greater than 1 (as shown in FIG. 2). Therefore, the optical sensor(s) 120 can simultaneously be used for frequencies including subharmonic imaging, fundamental imaging (FI), tissue harmonic imaging (THI), super-harmonic imaging (SHI), ultra-harmonic imaging (UHI), and subharmonic modes. However, in some variations, some or all of the transducer(s) 110 may additionally be used to detect some of the frequencies. A subset among the subharmonic imaging, FI, THI, SHI, and UHI modes can be selected depending on clinical applications. In some instances, the acousto-optic imaging system may only use FI and THI at the same time in a first type of imaging and use subharmonic and SHI modes in a second type of imaging. Similarly, the acousto-optic imaging system can also be used for only one of the subharmonic imaging, fundamental imaging (FI), tissue harmonic imaging (THI), super-harmonic imaging (SHI), or ultra-harmonic imaging (UHI) modes at any given time depending upon clinical applications.

Figure 4:
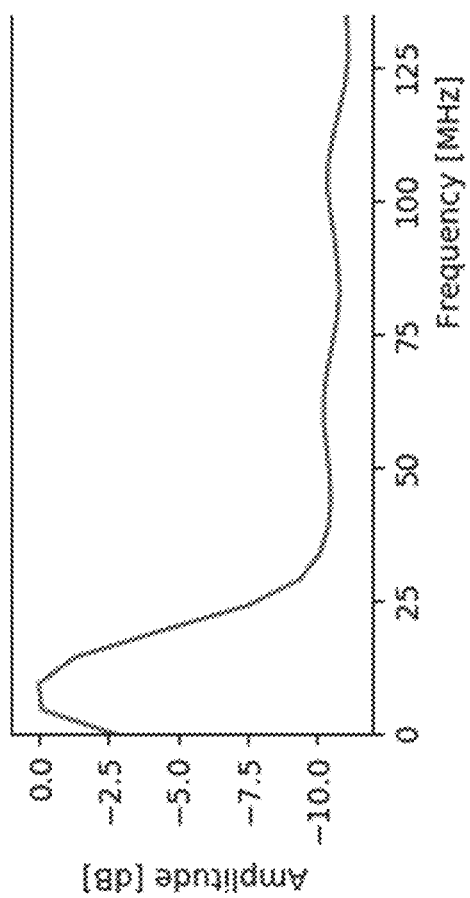
FIG. 4 illustrates an exemplary spectral response of an optical sensor in response to an ultrasound signal.

FIG. 4 illustrates an exemplary spectral response of an optical sensor to an ultrasound signal. An acousto-optic imaging system may include at least one transducer and at least one optical sensor (e.g., a whispering gallery mode (WGM) resonator) that is spectrally sensitive and have a broadband response. The at least one transducer may be configured to transmit ultrasound signals and the at least one optical sensor may be configured to receive ultrasound echoes in response to the ultrasound signals. The ultrasound signals may be characterized/described by a set of intensities and a set of fundamental frequencies $f_1$ (e.g., a first fundamental frequency $f_1$, a second fundamental frequency $f_1$, and/or the like). The optical sensor may receive the ultrasound echoes at ultrasound echo frequencies including the set of fundamental frequencies, a set of subharmonic frequencies of the set of fundamental frequencies, a set of super-harmonic frequencies of the set of fundamental frequencies, a set of ultra-harmonic frequencies of the set of fundamental frequencies, and/or a set of differential harmonics of the set of fundamental frequencies.

In some implementations, ultrasound contrast agents (e.g., gas microbubbles) may be introduced/injected in a blood vessel to increase signal reflection and/or improve contrast in ultrasound imaging. When insonated at the fundamental frequency f, the ultrasound contrast agents may help to better reflect an incoming ultrasound signal and also better generate nonlinear oscillations at harmonic and subharmonic frequencies. In some instances, while the tissue can also generate nonlinear oscillations at harmonic frequencies, the ability to generate signals at subharmonic frequencies (e.g., f/2) can be exclusive to ultrasound contrast agents. Because tissue does not generate subharmonic response, subharmonic imaging has been used as a method to isolate the signals from ultrasound contrast agents while suppressing signals from surrounding tissues. The suppression of signals of the surrounding tissue, however, may reduce the ability of sonographers to see anatomical and tissue landmarks. Therefore, the suppression of signals is generally known to limit use of subharmonic imaging as a primary imaging mode. The acousto-optic imaging system 101 using broadband and sensitive optical sensors can conveniently enable use of subharmonic imaging in addition to other imaging modalities described herein.

Thus, the optical sensor(s) 120 may be used to either replace transducer(s) 110 for detecting ultrasound, or may be combined with transducer(s) 110 for detecting ultrasound frequencies in an ultrasound imaging system. The one or more optical sensors 120 may have a bandwidth broad enough to detect all frequencies (f/M, . . . , f/2, f, 2f, 3f, 4f, 5f, . . . , Nf) where M and N are positive numbers including integers greater than 1. Some or all of these frequencies may be used for ultrasound imaging. For example, the one or more optical sensors 120 may be simultaneously used for subharmonic imaging, fundamental imaging, tissue harmonic imaging, ultra-harmonic imaging, and/or super-harmonic imaging for multiple dynamic imaging modes. Furthermore, the one or more optical sensors 120 may overcome the bandwidth limitations of transducer(s) 110 in differential tissue harmonic imaging and thus allows for a new imaging mode based on a combination of multiple fundamental frequencies (e.g., detection of the additional $f_2+f_1$ and $2f_2$ frequencies where $f_2+f_1$ are two different fundamental frequencies).

In other words, by leveraging the broadband response of the optical sensor(s) 120, acousto-optic imaging systems may enable imaging modes including fundamental frequencies, subharmonic frequencies, super-harmonic frequencies, ultra-harmonic frequencies, and/or differential frequencies, including new super-harmonic frequencies and differential-related frequencies not previously achievable with traditional ultrasound imaging systems. Therefore the acousto-optic imaging systems described herein may overcome bandwidth and sensitivity limitations of traditional acoustic imaging system (e.g., medical ultrasound imaging systems).

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. An acousto-optic imaging system comprising:
an ultrasound probe, comprising at least one transducer and at least one optical sensor, at least one optical sensor comprising ultrasound enhancement material;
the at least one transducer configured to transmit an ultrasound signal having a fundamental frequency f to a medium; and
the at least one optical sensor configured to produce one or more optical responses upon receiving harmonic and subharmonic ultrasound echoes, corresponding to the transmitted ultrasound signal, from the medium, the at least one optical sensor having a bandwidth greater than that of the at least one transducer, the bandwidth of the at least one optical sensor ranging from at least f/M to Nf, M and N being integers greater than 1.

2. The system of claim 1, wherein the at least one optical sensor is configured to produce at least one of the one or more optical responses upon receiving ultrasound echoes having a super-harmonic frequency of at least Qf, where Q is an integer 3 or greater.

3. The system of claim 1, wherein the at least one optical sensor is configured to produce at least one of the one or more optical responses upon receiving ultrasound echoes having a frequency of 2 for f.

4. The system of claim 1, wherein the at least one optical sensor is configured to produce at least one of the one or more optical responses upon receiving ultrasound echoes having a subharmonic frequency of f/R, where R is a number greater than 1.

5. The system of claim 1, wherein the fundamental frequency f is a first fundamental frequency $f_1$, and the at least one transducer is configured to generate a second ultrasound signal having a second fundamental frequency $f_2$.

6. The system of claim 5, wherein the at least one optical sensor is configured to produce at least one of the one or more optical responses upon receiving ultrasound echoes that correspond to a frequency of one or more linear combinations $nf_1+mf_2$, wherein n and m are integers such that $nf_1+mf_2$ is a positive number.

7. The system of claim 1, further comprising a computer-readable medium storing instructions to generate an image based on the one or more optical responses of the at least one optical sensor.

8. The system of claim 1, further comprising a computer-readable medium storing instructions to generate an image based on a change in the one or more optical responses of the at least one optical sensor.

9. The system of claim 8, wherein the change indicates a spectral shift and each optical response includes at least one spectral resonance feature with a full-width at half-maxima (FWHM) that is smaller than the spectral shift.

10. The system of claim 1, wherein the at least one optical sensor is configured to have an effective refractive index and a wall thickness that enable propagation of a set of whispering gallery modes (WGMs) in the at least one optical sensor.

11. The system of claim 10, wherein the at least one optical sensor is embedded in a polymer structure with an effective refractive index lower than the effective refractive index of the at least one optical sensor.

12. The acousto-optic imaging system of claim 1, wherein the ultrasound enhancement material comprises polyvinylidene fluoride, parylene, or polystyrene.

13. A method for acousto-optic imaging comprising:
providing an ultrasound probe, comprising at least one transducer and at least one optical sensor, at least one optical sensor comprising ultrasound enhancement material;
transmitting to a medium an ultrasound signal via the at least one transducer having a fundamental frequency f, and
producing one or more optical responses via the at least one optical sensor upon receiving harmonic and subharmonic ultrasound echoes, corresponding to the transmitted ultrasound signal, from the medium, the at least one optical sensor having a bandwidth greater than that of the at least one transducer, the bandwidth of the at least one optical sensor ranging from at least f/M to Nf, M and N being integers greater than 1.

14. The method of claim 13, wherein the at least one optical sensor is configured to produce at least one of the one or more optical responses upon receiving ultrasound echoes having a superharmonic frequency of at least Qf, where Q is an integer 3 or greater.

15. The method of claim 13, wherein the at least one optical sensor is configured to produce at least one of the one or more optical responses upon receiving ultrasound echoes having a frequency of 2f for f.

16. The method of claim 13, wherein the at least one optical sensor is configured to produce at least one of the one or more optical responses upon receiving ultrasound echoes having a subharmonic frequency of f/R, where R is an integer 2 or greater.

17. The method of claim 13, wherein the fundamental frequency f is a first fundamental frequency $f_1$, and the at least one transducer is configured to generate a second ultrasound signal having a second fundamental frequency $f_2$.

18. The method of claim 17, wherein the at least one optical sensor is configured to produce at least one of the one or more optical responses upon receiving ultrasound echoes that correspond to a frequency of one or more linear combinations $nf_1+mf_2$, wherein n and m are integers such that $nf_1+mf_2$ is a positive number.

19. The method of claim 13, further comprising:
generating, via a computer-readable medium, an image based on the one or more optical responses of the at least one optical sensor.

20. The method of claim 13, further comprising a computer-readable medium storing instructions to generate an image based on a change in the one or more optical responses of the at least one optical sensor, and wherein the change indicates a spectral shift and each optical response includes at least one spectral resonance feature with a full-width at half-maxima (FWHM) that is smaller than the spectral shift.

21. A method of acousto-optic imaging comprising:
providing at least one transducer, at least one optical sensor, and one or more optical detectors, at least one optical sensor comprising ultrasound enhancement material;
transmitting via the at least one transducer to a medium a ultrasound signal having a fundamental frequency f;
producing one or more optical responses via the at least one optical sensor upon receiving ultrasound echoes, corresponding to the ultrasound signal, from the medium, the received ultrasound echoes having a super-harmonic frequency, a subharmonic frequency and an ultra-harmonic frequency, the at least one optical sensor having a bandwidth greater than that of the one or more transducers, the bandwidth of the at least one optical sensor ranging from at least f/M to Nf, M and N being integers greater than 1;
detecting at least one change in the one or more optical responses via one or more optical detectors; and
generating an image of the medium based on the at least one change in the optical response.

* * * * *